United States Patent
Lai et al.

(10) Patent No.: US 11,229,413 B1
(45) Date of Patent: Jan. 25, 2022

(54) X-RAY CT APPARATUS WITH ADAPTIVE PHOTON COUNTING DETECTORS

(71) Applicant: CANON MEDICAL SYSTEMS CORPORATION, Otawara (JP)

(72) Inventors: Xiaochun Lai, Vernon Hills, IL (US); Liang Cai, Vernon Hills, IL (US); Yi Qiang, Vernon Hills, IL (US); Xiaohui Zhan, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 6 days.

(21) Appl. No.: 16/920,034

(22) Filed: Jul. 2, 2020

(51) Int. Cl.
*H01L 27/146* (2006.01)
*A61B 6/00* (2006.01)
*A61B 6/03* (2006.01)

(52) U.S. Cl.
CPC ............ *A61B 6/4241* (2013.01); *A61B 6/035* (2013.01); *A61B 6/54* (2013.01)

(58) Field of Classification Search
CPC ...... H01L 27/14612; H01L 31/035272; H04N 5/32; G01J 1/44; G01J 2001/444;
(Continued)

(56) References Cited

U.S. PATENT DOCUMENTS

2007/0120062 A1 5/2007 Li et al.
2008/0099689 A1 5/2008 Nygard et al.
(Continued)

FOREIGN PATENT DOCUMENTS

| EP | 3 510 928 A1 | 7/2019 |
|---|---|---|
| WO | WO 2008/054860 A2 | 5/2008 |
| WO | WO 2017/009736 A1 | 1/2017 |

OTHER PUBLICATIONS

S. Leng, R. Gutjahr, A. Ferrero, S. Kappler, A. Henning, A. Halaweish, W. Zhou, J. Montoya, C. McCollough, "Ultra-High Spatial Resolution Multi-Energy CT using Photon Counting Detector Technology." Proc SPIE Int. Soc Opt. Eng. Feb. 1, 2017; 10132: doi: 10.1117/12.2255589.

(Continued)

*Primary Examiner* — Don K Wong
(74) *Attorney, Agent, or Firm* — Oblon, McClelland, Maier & Neustadt, L.L.P.

(57) ABSTRACT

An embodiment of a computed tomography apparatus includes an x-ray source and scan control circuitry configured to control the x-ray source to expose a subject with x-rays over a scan having a plurality of views. A detector is disposed to receive x-rays from the x-ray source, has a plurality of anodes arranged in groups, and a common conductive strip between the anodes. Photon counting circuits are respectively provided for each of the anodes and have adjustable operating parameters. Connection circuitry is configured to adaptively connect, in a first mode, each anode to one of the photon counting circuits and, in a second mode, each anode in a group to a same one of the photon counting circuits. Processing circuitry, connected to the connection circuitry and the photon counting circuits, is configured to, for each of the views, select the first mode or the second mode and adjust the operating parameters based upon exposure data obtained from exposing the subject with the x-rays from the x-ray source.

20 Claims, 11 Drawing Sheets

(58) Field of Classification Search
CPC .... G01T 1/00; G01T 1/02; G01T 1/06; G01T 1/2018; G01T 1/20184; G01T 1/17; G01T 1/24; G01T 2/247; A61B 6/42; A61B 6/4208; A61B 6/40; A61B 6/4266; A61B 6/4233
See application file for complete search history.

(56) References Cited

U.S. PATENT DOCUMENTS

2009/0080601 A1   3/2009  Tkaczyk et al.
2016/0358957 A1* 12/2016  Guo ................ H01L 31/035272
2018/0206805 A1   7/2018  Onouchi

OTHER PUBLICATIONS

European Search Reported dated Nov. 2, 2021, issued in European Patent Application No. 21183401.5.

* cited by examiner

Adjustable CR-RC Shaper
through Adjusting Cp1, R1, Cp2 and R2

Adjustable Single-Line Delay Shaper

X-RAY CT APPARATUS WITH ADAPTIVE PHOTON COUNTING DETECTORS

FIELD

Embodiments described herein relate generally to an X-ray CT apparatus with photon counting detectors

BACKGROUND

Conventionally, in medical image systems, such as photon-counting type X-ray computed tomography (CT) apparatus, photon-counting type detectors are used to detect X-rays transmitted through the subject. Photon counting detectors are designed to record the energy of each incoming X-ray photon. In a typical CT scan environment, the photon counting detector is required to be able to record a high flux of incoming photons with good energy resolving accuracy. Direct-conversion type semiconductor detectors of cadmium telluride (CdTe), cadmium zinc telluride (CZT), or the like, or indirect-conversion type detectors of a scintillator, or the like, are used as a detector. An ASIC is typically used for the photon-counting CT which amplifies an output signal from the detector by using an amplifier, shapes its waveform, and then counts the number of incident X-ray photons of each of the windows, which are divided in accordance with the level of the signal.

The CdTe/CZT sensor is pixelated to a typical size between 250 um to 1 mm. As illustrated in FIG. 1, when an x-ray interacts within a pixel, induced signal is integrated to a charge sensitive preamplifier and the output of the charge preamplifier is passed to shaping, and then signal is compared with different thresholds. The energy range of x-ray is recorded at counters and arranged in bins.

During a CT scan, the flux varies dramatically not only in the spatial domain and but also time domain. The pixel configuration (pixel size or pitch size) and circuit parameters, i.e., decay constants of the preamplifier, shaping constants, and thresholds of the comparators, etc. significantly affect the performance of the detector. However, optimized parameters are not always the same. They are strongly dependent on x-ray flux and energy.

For example, a smaller pitch size design (<250 μm pitch) is preferred for high flux case since it is relatively immune to pulse-pile up problem. However, this design would at the same time degrade the detector response as severe charge sharing, and cross talk effect can happen in such case. The charge loss between the small pitches is another degradation factor. Larger pitch size (~500 μm) tends to produce less charge sharing and cross talk effect, leading to better detector response. But the larger pitch size detector has a strong pule-pile up problem in the high flux region. Studies have shown that from a material decomposition noise point of view, smaller pitch size (e.g. <250 μm) is preferred in high flux scenario. However, large pitch size (e.g. ~500 μm) is preferred in low flux region.

The preamplifier parameters also have an effect on the photon counting. For accurate energy information, it is preferred to have longer signal integration times for an active reset-type preamplifier or a longer decay constant for a feedback resistor-type preamplifier. However, the longer integration time or decay constant is not preferred when the x-ray flux is high, as more pile-up will degrade the detector performance. A longer time for shaping is also preferred for more accurate energy information but is also subject to pile-up problems. Lastly, optimizing the thresholds in the signal counting can significantly increase the signal-to-noise ratio. The optimum thresholds are, however, highly dependent upon the x-ray flux and spectrum.

One approach is to use uniform and fixed small pixel (225-500 μm) pattern design with the readout electronics, including the preamplifier and shaping electronics, optimized for high flux. The comparator thresholds are optimized for a specific case. This design can handle the high flux situation, but performance is degraded by charge-sharing and cross-talk.

To address spatial non-uniformity in the x-ray flux, a detector in U.S. Pat. No. 7,916,836 was proposed having a non-uniform pixel pattern. In a high flux exposure, the detector is configured through switching with small pixels (FIG. 6), while in the low flux exposure, the detector is configured with large pixels (FIG. 7). However, the x-ray flux varies in both the spatial and time domains. In one CT scan the same detector can be exposed to high flux in one view and low flux in another. The flux also can change scan to scan. The detector in U.S. Pat. No. 7,916,836 is changed based upon examination protocols or patient size and is not able to change the pixel pattern in real time to adapt to the changing flux.

In U.S. Pat. No. 7,488,945 pixel arrangements can be adaptively set according to a detected count rate in the previous views. This allows a detector to adjust the pixel configuration using the data of the previous view. But such adjusting may not be fast enough as the flux (count rate) can change dramatically between two sequential views. Further, the charge loss at streets between subpixels cannot be avoided. Also, both U.S. Pat. Nos. 7,916,836 and 7,488,945 do not adaptively optimizing operation parameters of readout electronics based on the count rate and the spectrum. They are critical factors affecting the photon counting detector and CT performance and also can vary between in both spatial and time domain.

Another approach to addressing the high flux and non-uniformity issues involved a two-layer detector where the first layer absorbs 90-99% of the flux and the second layer absorbs the remainder. This system is illustrated in U.S. Pat. No. 7,606,347. The design involves monitoring subpixels in the first layer, inhibiting signals from saturated subpixels, and compensating for the inhibited signals by the second layer detector. The system is complicated and costly to manufacture.

DETAILED DESCRIPTION

Figure 1:
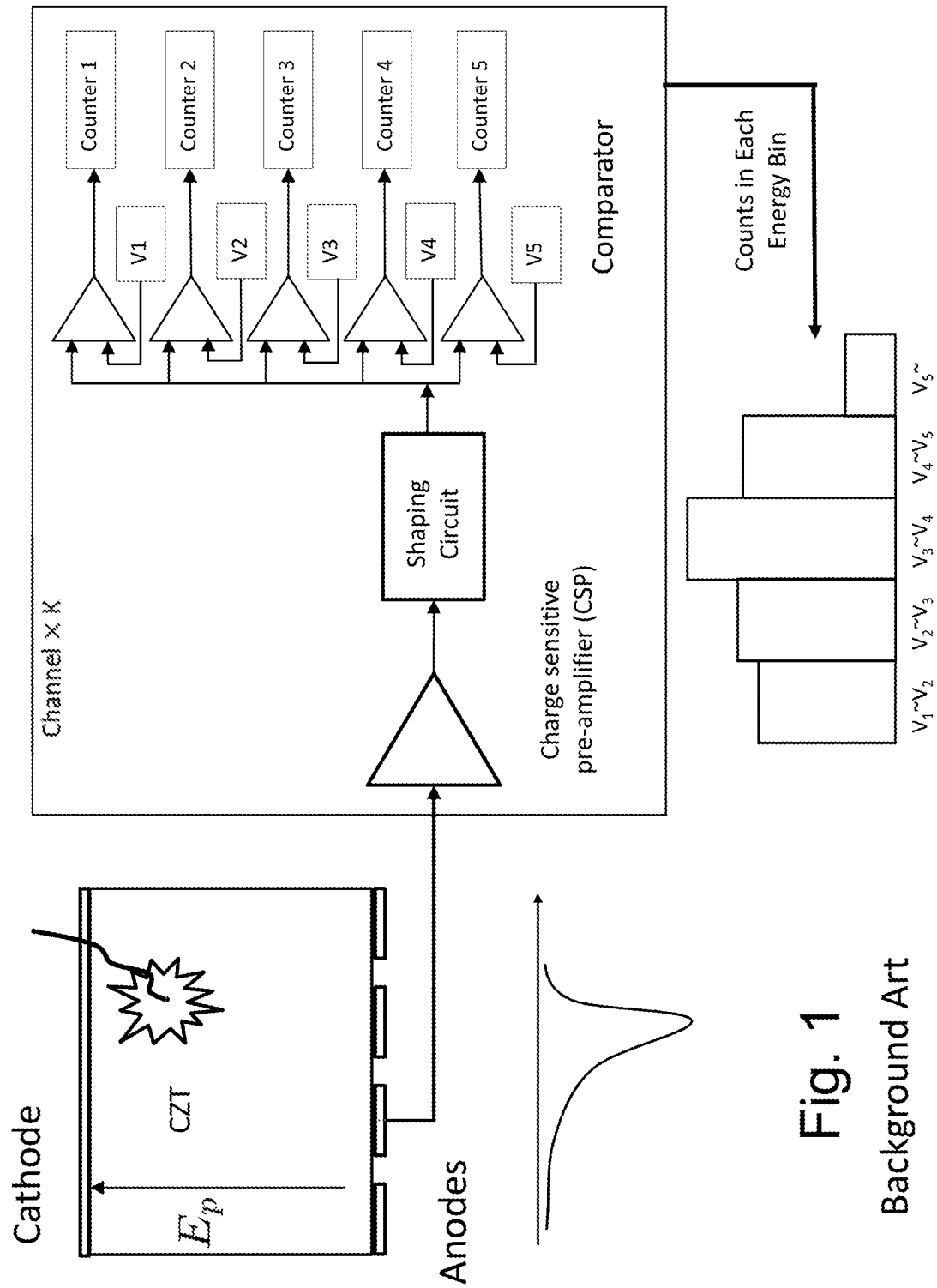
FIG. 1 is a diagram illustrating conventional photon counting circuitry.
Figure 2:
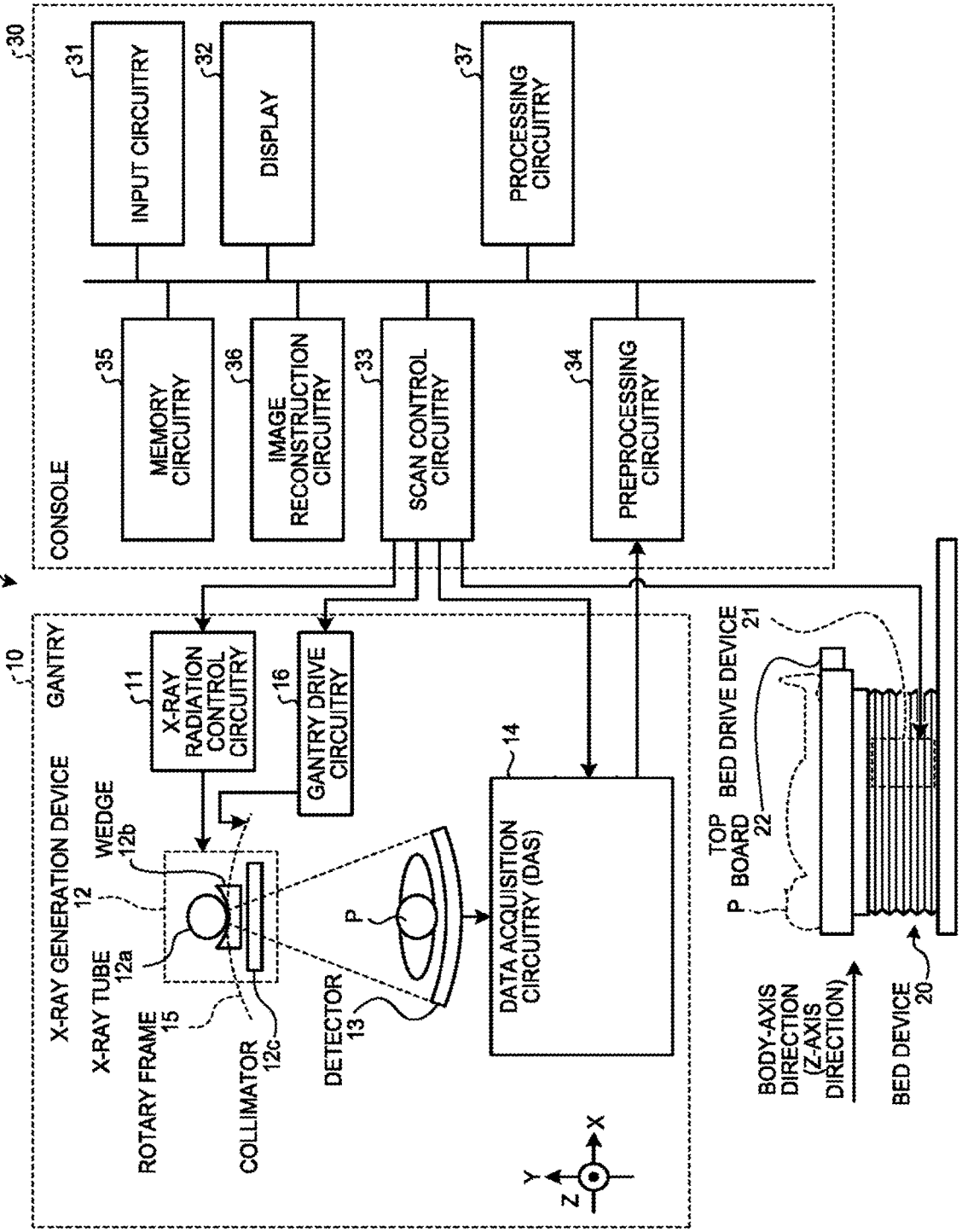
FIG. 2 is a diagram illustrating an example of the configuration of a photon-counting type X-ray CT apparatus according to a first embodiment.

With reference to the accompanying drawings, a detailed explanation is given below of an embodiment of a data acquisition device and an X-ray CT apparatus. Furthermore, in the following embodiment, an explanation is given by using, for example, a photon-counting type X-ray CT apparatus as the X-ray CT apparatus First Embodiment First, an explanation is given of an embodiment of the photon-counting type X-ray CT apparatus. FIG. 2 is a diagram that illustrates an example of the configuration of a photon-counting type X-ray CT apparatus 1 according to a first embodiment. As illustrated in FIG. 2, the photon-counting type X-ray CT apparatus 1 according to the first embodiment includes a gantry 10, a bed device 20, and a console 30.

The gantry 10 is a device that emits X-rays to a subject P (patient), detects the X-rays that are transmitted through the subject P, and outputs them to the console 30, and it includes X-ray radiation control circuitry 11, an X-ray generation device 12, a detector 13, data acquisition circuitry (DAS: Data Acquisition System) 14, a rotary frame 15, and gantry drive circuitry 16.

The rotary frame 15 is an annular frame that supports the X-ray generation device 12 and the detector 13 such that they are opposed to each other with the subject P interposed therebetween and that is rotated at high speed in a circular orbit around the subject P by the gantry drive circuitry 16 that is described later.

The X-ray radiation control circuitry 11 is a device that serves as a high-voltage generation unit and supplies a high voltage to an X-ray tube 12a, and the X-ray tube 12a generates X-rays by using the high voltage that is supplied from the X-ray radiation control circuitry 11. Under the control of scan control circuitry 33, which is described later, the X-ray radiation control circuitry 11 adjusts the tube voltage or the tube current that is supplied to the X-ray tube 12a, thereby adjusting the amount of X-rays that are emitted to the subject P.

Furthermore, the X-ray radiation control circuitry 11 switches a wedge 12b. Furthermore, the X-ray radiation control circuitry 11 adjusts the numerical aperture of a collimator 12c, thereby adjusting the radiation range (the fan angle or the cone angle) of X-rays. Moreover, according to the present embodiment, there may be a case where multiple types of wedges are manually switched by an operator.

The X-ray generation device 12 is a device that generates X-rays and emits the generated X-rays to the subject P, and it includes the X-ray tube 12a, the wedge 12b, and the collimator 12c.

The X-ray tube 12a is a vacuum tube that emits X-ray beams to the subject P by using the high voltage that is supplied by the X-ray radiation control circuitry 11, and it emits X-ray beams to the subject P in accordance with the rotation of the rotary frame 15. The X-ray tube 12a generates X-ray beams that spread with the fan angle and the cone angle. For example, under the control of the X-ray radiation control circuitry 11, the X-ray tube 12a is capable of continuously emitting X-rays all around the subject P for a full reconstruction or continuously emitting X-rays for a half reconstruction within an emission range (180°+the fan angle) that enables a half reconstruction. Furthermore, under the control of the X-ray radiation control circuitry 11, the X-ray tube 12a is capable of intermittently emitting X-rays (pulse X-rays) at a previously set position (tube position). Furthermore, the X-ray radiation control circuitry 11 is capable of changing the intensity of X-rays, emitted from the X-ray tube 12a. For example, the X-ray radiation control circuitry 11 increases the intensity of X-rays, emitted from the X-ray tube 12a, at a specific tube position, and it decreases the intensity of X-rays, emitted from the X-ray tube 12a, in the area other than the specific tube position.

The wedge 12b is an X-ray filter that adjusts the amount of X-rays with regard to the X-rays that are emitted from the X-ray tube 12a. Specifically, the wedge 12b is a filter that transmits and attenuates X-rays, emitted from the X-ray tube 12a, such that X-rays, emitted from the X-ray tube 12a to the subject P, has a predetermined distribution. For example, the wedge 12b is a filter that is obtained by processing aluminum so as to have a predetermined target angle or a predetermined thickness. Furthermore, the wedge is also called a wedge filter or a bow-tie filter.

The collimator 12c is a slit that narrows the irradiation range of X-rays, of which the amount of X-rays has been adjusted by the wedge 12b, under the control of the X-ray radiation control circuitry 11 that is described later.

The gantry drive circuitry 16 drives and rotates the rotary frame 15 so that the X-ray generation device 12 and the detector 13 are rotated in a circular orbit around the subject P.

Each time an X-ray photon enters, the detector 13 outputs the signal with which the energy value of the X-ray photon may be measured. The X-ray photon is, for example, an X-ray photon that is emitted from the X-ray tube 12a and is transmitted through the subject P. The detector 13 includes multiple detection elements that output an electric signal (analog signal) of 1 pulse each time an X-ray photon enters. The photon-counting type X-ray CT apparatus 1 counts the number of electric signals (pulses) so as to count the number of X-ray photons that enter each of the detection elements. Furthermore, the photon-counting type X-ray CT apparatus 1 performs arithmetic processing on the signal so as to measure the energy value of the X-ray photon that causes output of the signal.

The above-described detection element includes, for example, a scintillator and an optical sensor, such as a photomultiplier tube. In such a case, the detector 13, illustrated in FIG. 2, is an indirect-conversion type detector that converts the incident X-ray photon into scintillator light by using the scintillator and converts the scintillator light into an electric signal by using the optical sensor, such as a photomultiplier tube. Furthermore, there may be a case where the above-described detection element is a semiconductor device of, for example, cadmium telluride (CdTe), cadmium zinc telluride (CdZnTe), or the like. In such a case, the detector 13, illustrated in FIG. 2, is a direct-conversion type detector that directly converts the incident X-ray photon into an electric signal.

For example, the detector 13, illustrated in FIG. 2, is a plane detector in which detection elements are arranged in N columns in the channel direction (the direction of the X axis in FIG. 2) and in M columns in the direction of the rotational center axis of the rotary frame 15 (the direction of the Z axis in FIG. 2) where the gantry 10 is not tilted. When a photon enters, the detection element outputs an electric signal of 1 pulse. The photon-counting type X-ray CT apparatus 1 discriminates among individual pulses that are output from a detection element 131, thereby counting the number of X-ray photons that enter the detection element 131. Furthermore, the photon-counting type X-ray CT apparatus 1 performs arithmetic processing based on the intensity of a pulse, thereby measuring the energy value of the counted X-ray photon.

The data acquisition circuitry 14 is a data acquisition system (DAS), and it acquires the detection data on X-rays that are detected by the detector 13. For example, the data acquisition circuitry 14 generates the count data that is obtained by counting the photons (X-ray photons), which come from the X-ray that is transmitted through the subject, for each energy band, and it transmits the generated count data to the console 30 that is described later. For example, if X-rays are continuously emitted from the X-ray tube 12a while the rotary frame 15 is rotated, the data acquisition circuitry 14 acquires the group of count data for the entire periphery (360 degrees). The data acquisition circuitry 14 also can acquire data for each view. Furthermore, the data acquisition circuitry 14 transmits each acquired count data in relation to the tube position to the console 30 that is described later. The tube position is the information that indicates the projection direction of the count data.

The bed device 20 is a device on which the subject P is placed and, as illustrated in FIG. 2, it includes a bed drive device 21 and a top board 22. The bed drive device 21 moves the top board 22 in the direction of the Z axis to move the subject P into the rotary frame 15. The top board 22 is a board on which the subject P is placed. Furthermore, in the present embodiment, an explanation is given of a case where the relative position between the gantry 10 and the top board 22 is changed by controlling the top board 22; however, this is not a limitation on the embodiment. For example, if the gantry 10 is self-propelling, the relative position between the gantry 10 and the top board 22 may be changed by controlling driving of the gantry 10.

Furthermore, for example, the gantry 10 conducts helical scan to scan the subject P in a helical fashion by rotating the rotary frame 15 while the top board 22 is moved. Alternatively, the gantry 10 conducts conventional scan to scan the subject P in a circular orbit by rotating the rotary frame 15 with the position of the subject P fixed after the top board 22 is moved. Alternatively, the gantry 10 implements a step-and-shoot method to conduct conventional scan at multiple scan areas by moving the position of the top board 22 at a constant interval.

The console 30 is a device that receives an operation of the photon-counting type X-ray CT apparatus 1 from an operator and that reconstructs X-ray CT image data by using the projection data that is acquired by the gantry 10. As illustrated in FIG. 2, the console 30 includes input circuitry 31, a display 32, the scan control circuitry 33, preprocessing circuitry 34, memory circuitry 35, image reconstruction circuitry 36, and processing circuitry 37.

The input circuitry 31 includes a mouse, keyboard, trackball, switch, button, joystick, or the like, which is used by an operator of the photon-counting type X-ray CT apparatus 1 to input various commands or various settings, and it transfers the information on the command or setting, received from the operator, to the processing circuitry 37. For example, the input circuitry 31 receives, from an operator, a capturing condition for X-ray CT image data, a reconstruction condition for reconstructing X-ray CT image data, an image processing condition for X-ray CT image data, or the like.

The display 32 is a monitor that is viewed by an operator and, under the control of the processing circuitry 37, it displays the image data, generated from X-ray CT image data, to the operator or displays a graphical user interface (GUI) for receiving various commands, various settings, or the like, from the operator via the input circuitry 31.

The scan control circuitry 33 controls operations of the X-ray radiation control circuitry 11, the gantry drive circuitry 16, the data acquisition circuitry 14, and the bed drive device 21 under the control of the processing circuitry 37, thereby controlling data acquisition processing by the gantry 10. For example, scan control circuitry 33 sends sequence control commands to data acquisition circuitry 14 to control exposure operations, as discussed in more detail below.

The preprocessing circuitry 34 performs correction processing, such as logarithmic conversion processing, offset correction, sensitivity correction, or beam hardening correction, on the count data that is generated by the data acquisition circuitry 14, thereby generating corrected projection data.

The memory circuitry 35 stores the projection data that is generated by the preprocessing circuitry 34. Furthermore, the memory circuitry 35 stores the image data, or the like, which is generated by the image reconstruction circuitry 36 that is described later. Moreover, the memory circuitry 35 appropriately stores processing results of the processing circuitry 37 that is described later.

The image reconstruction circuitry 36 reconstructs X-ray CT image data by using the projection data that is stored in the memory circuitry 35. Here, the reconstruction method includes various methods, and it may be, for example, back projection processing. Furthermore, the back projection processing may include, for example, back projection processing by using a filtered back projection (FBP) method. Alternatively, the image reconstruction circuitry 36 may also use a successive approximation technique to reconstruct X-ray CT image data. Furthermore, the image reconstruction circuitry 36 conducts various types of image processing on X-ray CT image data, thereby generating image data. Then, the image reconstruction circuitry 36 stores, in the memory circuitry 35, the reconstructed X-ray CT image data or the image data that is generated during various types of image processing.

The processing circuitry 37 controls operations of the gantry 10, the bed device 20, and the console 30 so as to perform the overall control on the photon-counting type X-ray CT apparatus 1. Specifically, the processing circuitry 37 controls the scan control circuitry 33 so as to control CT scan that is conducted by the gantry 10. Furthermore, the processing circuitry 37 controls the image reconstruction circuitry 36 so as to control image reconstruction processing or image generation processing by the console 30. Furthermore, the processing circuitry 37 performs control such that various types of image data, stored in the memory circuitry 35, are displayed on the display 32.

Heretofore, the overall configuration of the photon-counting type X-ray CT apparatus 1 according to the first embodiment is explained. Here, each processing function, performed by each of the above-described circuitry, is stored in the memory circuitry 35 in the form of the program that is executable by the computer. Furthermore, each circuitry reads and executes each program from the memory circuitry 35, thereby performing the above-described various functions.

In one example, programs corresponding to the operations of the data acquisition circuitry 14 are stored in the memory circuitry 35 in the form of a program that is executable by a computer. Processor 37 executes the programs for data acquisition circuitry 14 and sends instructions to and controls data acquisition circuitry 14 to acquire data as well as controls the transfer data from data acquisition circuitry 14. In a second example, data acquisition circuitry 14 includes a processor that reads and executes each program from the memory circuitry 35 to implement the function that corresponds to each program.

Furthermore, the word "processor", used in the above explanations, means for example a central processing unit (CPU), a graphics processing unit (GPU), or a circuit, such as an application specific integrated circuit (ASIC), or a programmable logic device (e.g., a simple programmable logic device: SPLD, a complex programmable logic device: CPLD, or a field programmable gate array: FPGA). The processor reads and executes the program, stored in the memory circuitry, to perform the function. Furthermore, a configuration may be such that, instead of storing a program in the memory circuitry, a program is directly installed in a circuit of the processor. In this case, the processor reads and executes the program, installed in the circuit, to perform the function. Furthermore, with regard to the processors according to the present embodiment, instead of the case where each processor is configured as a single circuit, multiple independent circuits may be combined to be configured as a single processor to implement the function.

With the above-described configuration, the photon-counting type X-ray CT apparatus 1 according to the first embodiment allows an improvement in the image acquisition due to the operation of the data acquisition circuitry 14 that optimizes data acquisition based upon energy and flux, which is described in detail below. A diagram of the data acquisition circuitry 14 is provided in FIG. 3. A group of anodes in the detector is shown at 40. The anodes 40-1 to 40-4 have a typical size of 500 um or less. These anodes are selectively grouped to form one large pixel and are individually used as plural small pixels. In this example, four adjacent anodes 40-1 to 40-4 arranged in a rectangular group are combined to form a large pixel and each individual anode forms a small pixel. Other arrangements and numbers of anodes could be grouped together to form the large pixel. For example, 1×2, 1×4 or 3×3 groups of anodes are possible.

A street is formed between the anodes and is typically 10 um to 50 um wide. In the center of the street, there is common conductive strip 40-5 with a typical size of 5 um to 45 um, which has lower voltage compared to anodes 40-1 to 40-4. It prevents the charge generated by x-ray from being trapped in the street. The anode is typically grounded to 0 V and the strip is typically biased in the range of 0V to −100V.

The outputs of the anodes are connected to switching circuit 41. Switching circuit 41 connects one of anodes 40-1 to 40-4 to a respective one of the adjustable photons counting circuits 42-1 to 42-4 when the switches 44 are in the upper position. The data from each anode is collected individually by adjustable photon counting circuits 42-1 to 42-4. Switching circuit 41 connects all of the anodes to adjustable photon counting circuit 42-5 when the switches 44 are in the lower position, aggregating the individual anodes to one large pixel where the data is collected together.

The adjustable photon counting circuits 42-1 to 42-5 count the photons and collect the photon counts into energy bin to generate collected data. The collected data is output to processing circuit 43.

Processing circuit 43 receives, analyzes and stores, in storage 45, the collected data in both of sense and exposure operations. Storage 45 may be any type of memory such as a RAM or NAND. The processing circuit receives data from the sensing operation to determine the flux of the x-ray signal and generate a switching signal and one or more parameter signals for optimal data collection. After the sensing operation, the exposure operation takes place where the anodes are optimally configured as a small or large pixel and the adjustable photon counting circuits 42-1 to 42-5 have optimal settings to collect the exposure data.

Processing circuit 43 generates the switching signal to control switching circuit 41 to appropriately connect the anodes 40-1 to 40-4 as individual (small) pixels or one large pixel, and generates one or more parameter signals to adjust the operation of adjustable photon counting circuits 42-1 to 42-5. It is noted that while the parameter signal line is shown as a single contact with circuits 42-1 to 42-4, each of circuits 42-1 to 42-4 is connected to the parameter signal line to receive the parameter signal or signals. The processing 43 will be described in more detail below.

Figure 3:
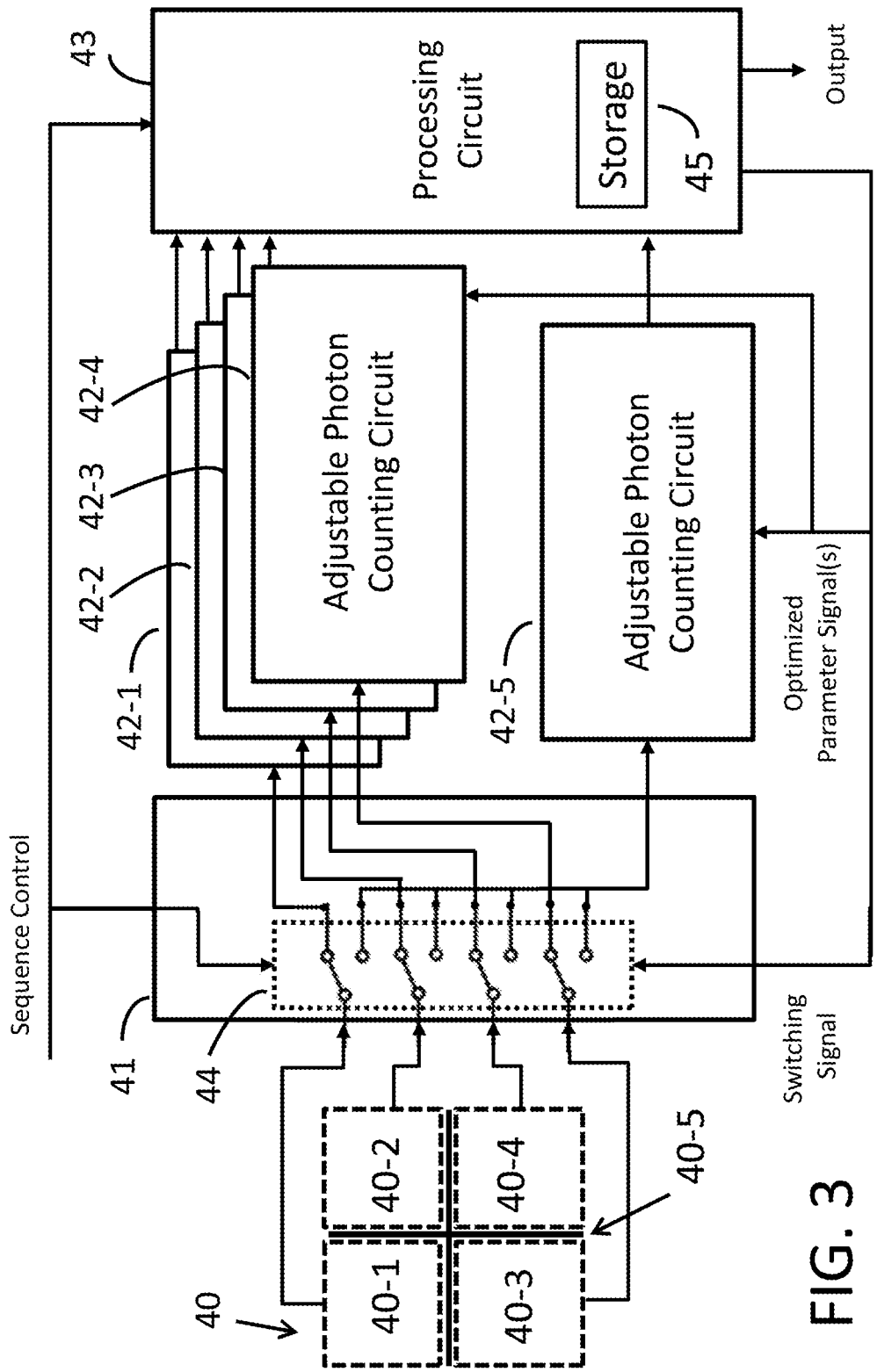
FIG. 3 is a diagram illustrating an embodiment of the data acquisition circuitry according to the invention.
Figure 4:
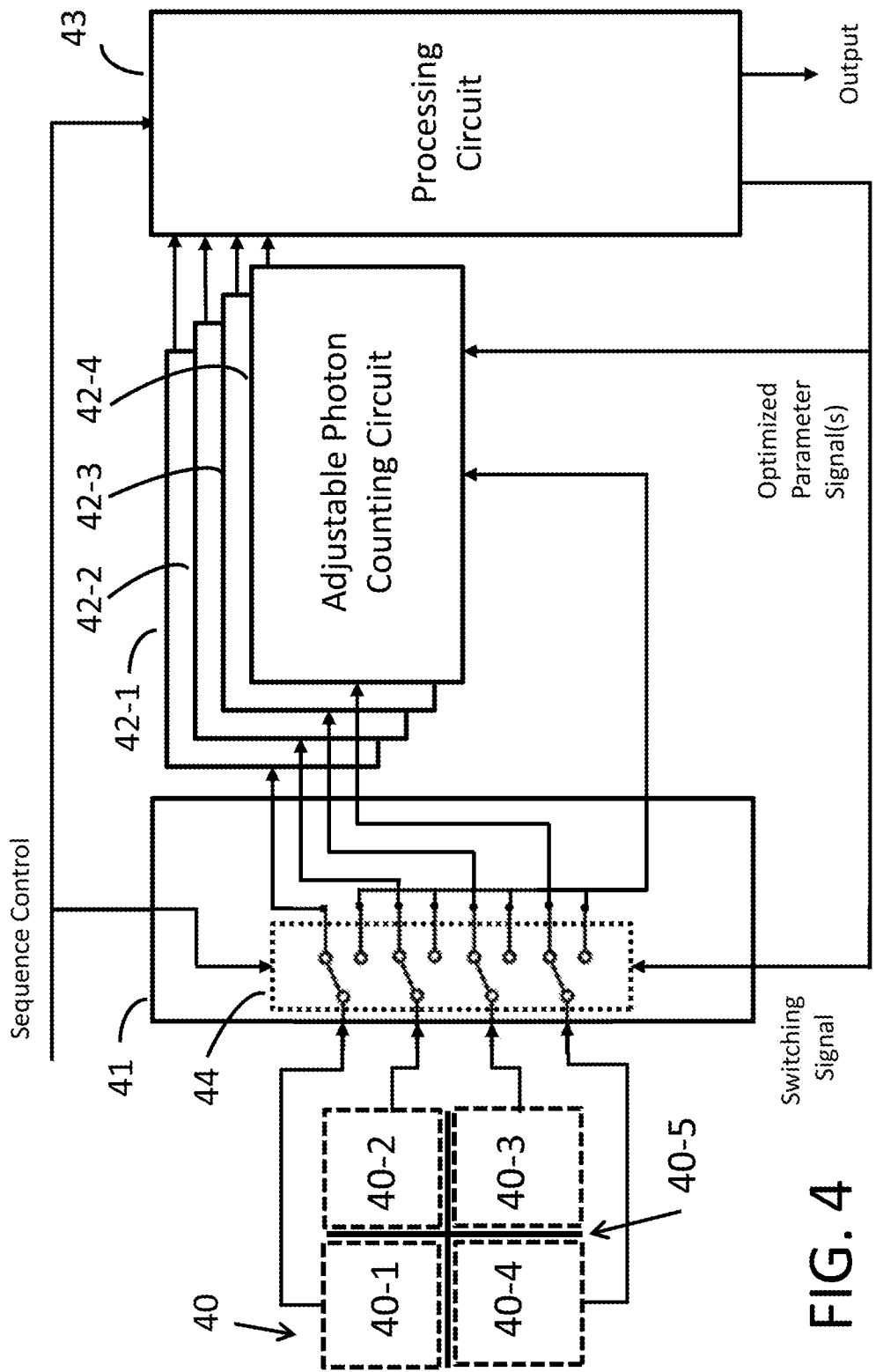
FIG. 4 is a diagram illustrating a modification of the embodiment of the data acquisition circuitry of FIG. 3.

A modification of the circuit of FIG. 3 is shown in FIG. 4. There are only four adjustable photon counting electronics 42-1 to 42-4 and circuit 42-4 collects both the data from anode 40-4 when the circuit is connected in the individual anode mode (small size pixel) and the data from all of anodes 40-1 to 40-4 when the circuit is connected in the large pixel mode. This modification has fewer adjustable photon counting circuits resulting in a simpler and less expensive design.

Figure 5:
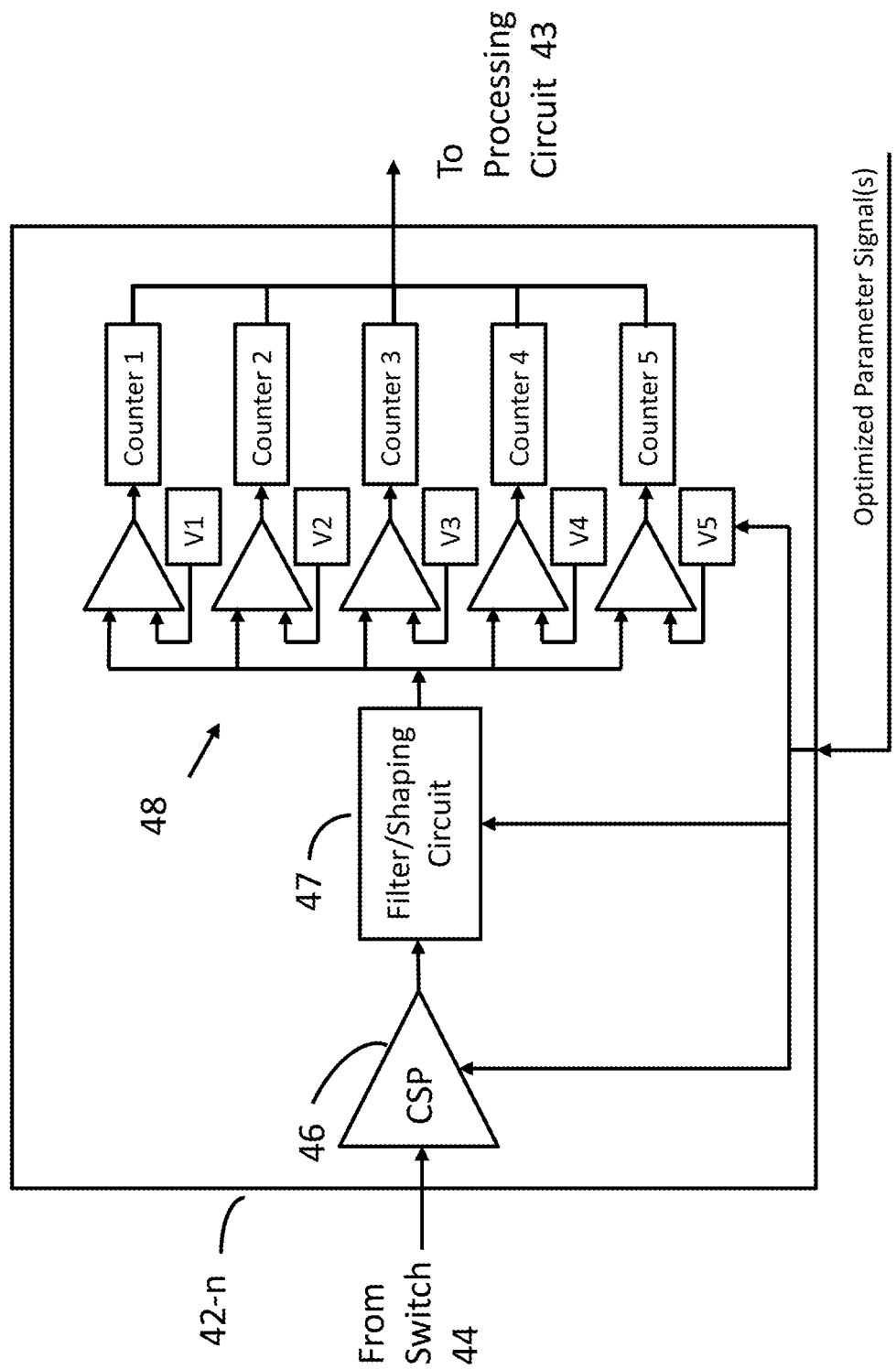
FIG. 5 is a diagram illustrating an adjustable photon counting circuit according to the invention.

FIG. 5 shows the adjustable photon counting electronics 42-1 to 42-5 in more detail. A charge sensitive preamplifier (CSP) 46 (Details are discussed below with respect to FIGS. 6A and 6B) receives the current output of one of the pixels generated by a photon and this current is accumulated in the feedback capacitors (Cp) of CSP and converted to a voltage signal output. The signal output by CSP 46 is input to shaping circuit 47 which turns the signal to desired shapes, typically with a reduced pulse width but the preserved energy information of the signal. The desired shapes are discussed below with respect to FIGS. 7A and 7B.

The signal output from the shaping circuit 47 is input to a comparator 48 having a plurality of comparing circuits each comparing the shaped signal to a reference voltage generated by reference voltage circuits V1-V5. The reference voltages are chosen to arrange the number of counts into energy bins representing the energy of the signal output by shaping circuit 47. In this embodiment, five comparing circuits compare the signal output by shaping circuit 47 to reference voltages of reference voltage circuits V1-V5, respectively, and the five counters record the number of times the shaping signal has a voltage value in the respective energy bins. The present invention is not limited to 5 comparing circuits. Other numbers of comparing and reference voltage circuits may be used based upon system requirements and design.

The parameter signals may also include a setting value for the reference voltage circuits V1-V5. The voltages of the reference voltage circuits V1-V5 are optimally set to collect the data based upon the results of the sensing operation.

Figure 6A:
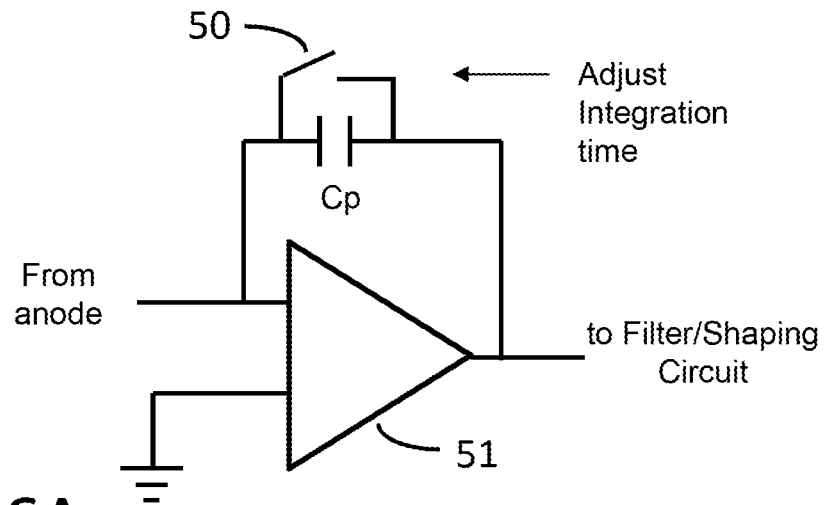
FIG. 6A is a diagram illustrating an example of the charge sensitive pre-amplifier (CSP) of FIG. 5.
Figure 6B:
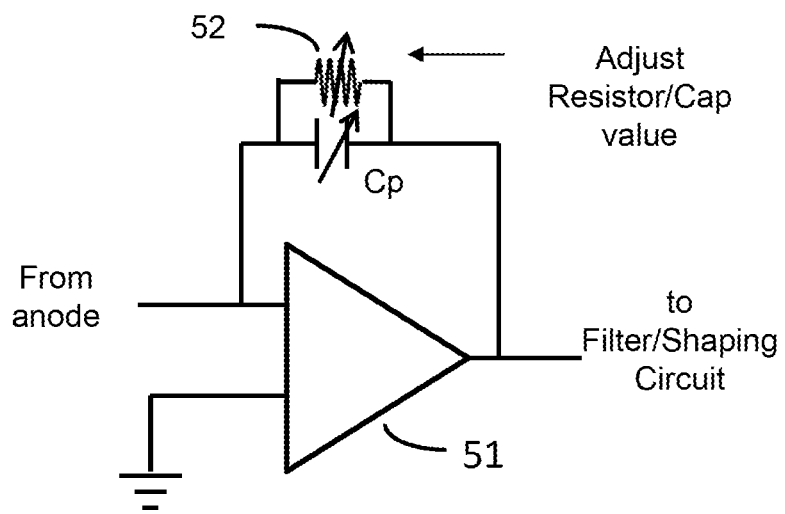
FIG. 6B is a diagram illustrating another example of the CSP of FIG. 5.

FIGS. 6A and 6B show two examples of the CSP circuit 46. FIG. 6A shows an active reset type CSP and FIG. 6B shows a feedback resistor type CSP. To get accurate energy information, it is preferred to have a longer signal integration time. On the other hand, longer integration time is not preferable when x-ray flux is high, given that more pile-up will degrade the detector performance.

In FIG. 6A, the switch is open during the charge integration period and the switch 50 is closed to reset the amplifier 51. The appropriate time is in the range of 5 ns to 100 ns and is chosen based upon the flux and energy readings from the sensing operation. For FIG. 6B, the value of variable resistor 52 is chosen to set the appropriate decay constant (R*Cp), which is in the range of 5 ns to 100 ns. Sensing circuit 43 outputs parameter signals to appropriately set the integration time or decay constant. The present invention is not limited to these two types preamplifiers and other types of preamplifiers, such as periodically reset preamplifiers, may be used depending upon system requirements and design.

Figure 7A:
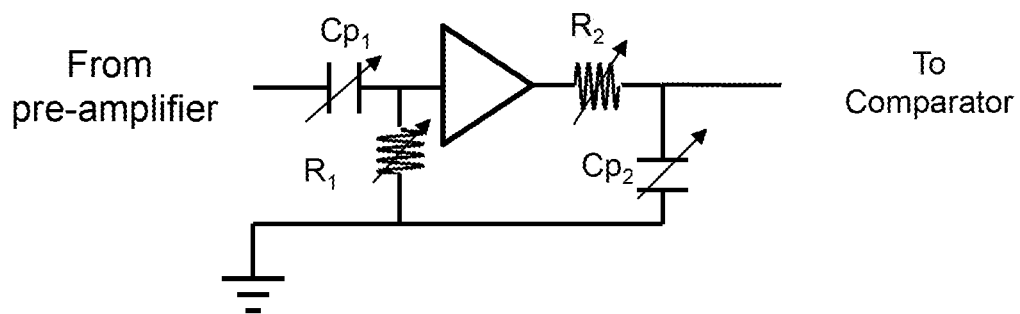
FIG. 7A is a diagram illustrating an example of a signal shaping circuit according to the invention.
Figure 7A:
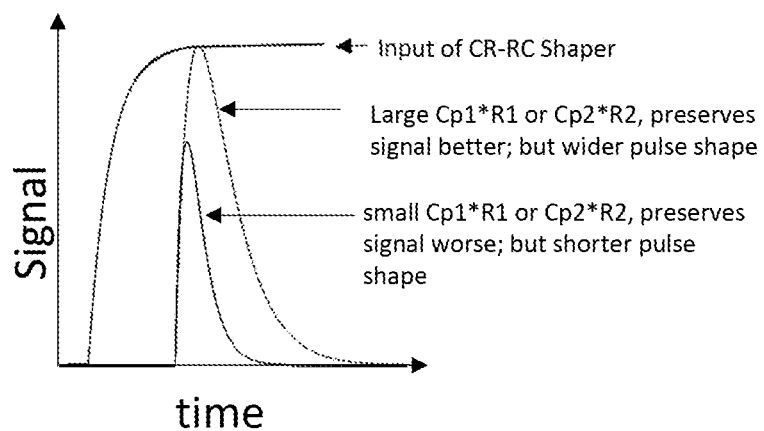
Figure 7B:
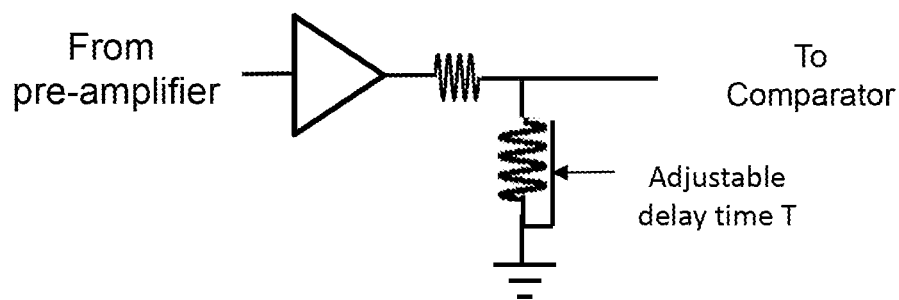
FIG. 7B is a diagram illustrating another example of the signal shaping circuit according to the invention.
Figure 7B:
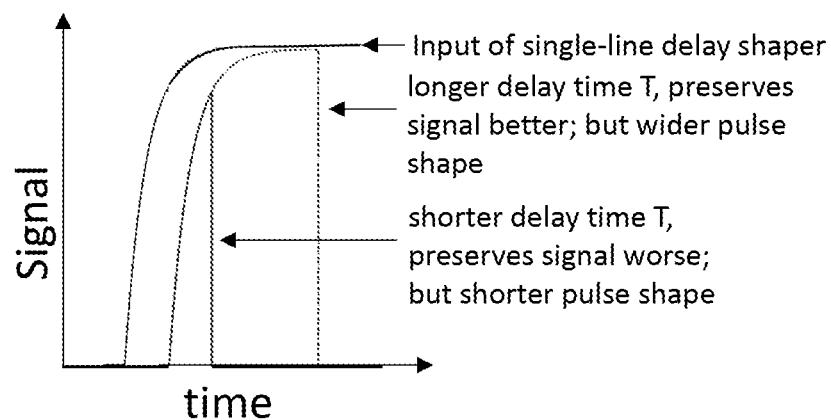

FIG. 7A and FIG. 7B show two examples of shaping circuit 46. FIG. 7A shows an adjustable CR-RC shaper and FIG. 7B shows an adjustable single-line delay shaper. To get accurate energy information, it is preferred to have a wider pulse width (longer shaping time). On the other hand, wider pulse width is not preferable when x-ray flux is high, given that more pile-up will degrade the detector performance.

In FIG. 7A, the value of the variable resistor ($R_1$ and $R_2$) is chosen to set an appropriate shaping width, which is determined by $Cp_1*R_1$ and $Cp_2*R_2$, based on the flux and energy reading from the sensing operation. Eva and E are the signals before and after the shaping respectively, and are given as $$E_{out} = \frac{EC_{p1}R_1}{C_{p1}R_1 - C_{p1}R_1}\left[e^{-\frac{t}{C_{p1}R_1}} - e^{\frac{t}{C_{p2}R_1}}\right],$$

where t is time.

Similarly, in FIG. 7B, the value of the variable delay time T is chosen to be set appropriately based on the flux and energy reading from the sensing operation. The present invention is not limited to these two types preamplifiers and other types of preamplifiers, such as a multiple stage CR-$RC^n$ shaper or multiple line delay shaper, active pulse shaper, triangular shaper and trapezoidal shaper, may be used based upon system requirements and design. The key feature of the shaping circuit according to the invention is that the shaping parameters of these shapers can be adjusted based input x-ray flux and energy.

FIGS. 7A and 7B each show the original signal and two shaped signals. The longer delay time preserves the signal shape better but has a wider pulse width. The shorter delay time has the advantage of a shorter pulse width but preserves the signal worse.

Figure 8:
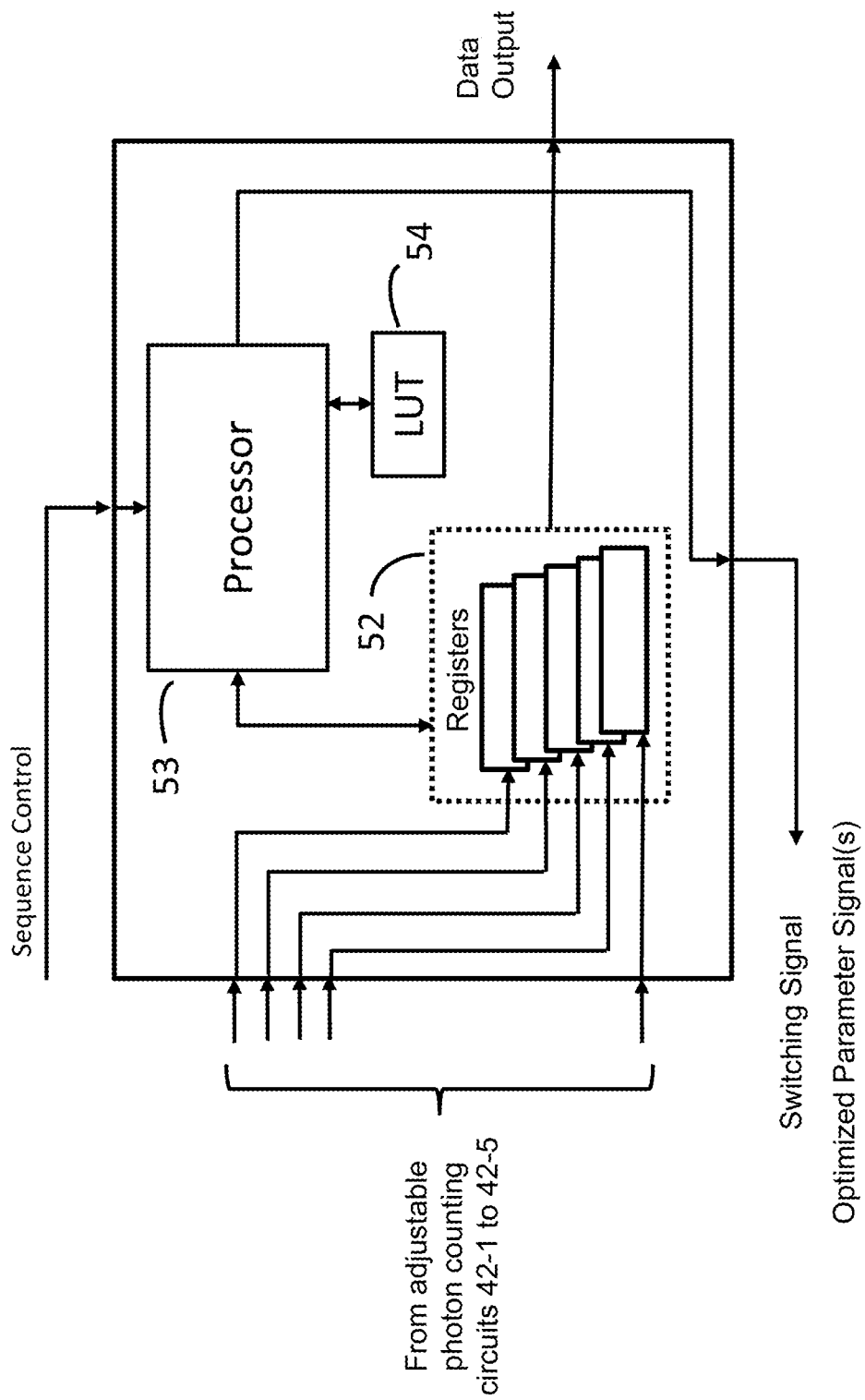
FIG. 8 is a diagram illustrating an embodiment of the processing circuit according to the invention.

The processing circuit 43 is shown in more detail in FIG. 8. Circuit 43 includes a processor 53 connected to a set of registers 52 and a LUT 54. The LUT stores optimal settings for the anodes, CSP, signal shaping circuit, and reference voltage levels as a function of energy and flux values.

In one embodiment, the optimal settings are precalculated by the following method:

$$\hat{x} = \underset{x}{\operatorname{argmin}}\{\phi(x|f)\}$$

where $\hat{x}=[\hat{x}_1, \hat{x}_2, \hat{x}_3, \hat{x}_4]$ is the optimized settings for the anodes ($\hat{x}_1$), CSP ($\hat{x}_2$), signal shaping ($\hat{x}_3$) and the comparators' thresholds ($\hat{x}_4$). It will minimize the object function $\phi(x|f)$ with given input, $(f=[f_1,f_2])$ where $f_1$ is x-ray flux and $f_2$, a metric indicating whether the spectrum is soft or hard, such as ratio between the number of low and high energy x-rays. The object function ($\phi(x|f)$) can be specifically designed base on system and design requirement, such as material decomposition variance, material decomposition bias, or mean square error.

The precalculated optimized parameters $\hat{x}=[\hat{x}_1,\hat{x}_2, \hat{x}_3, \hat{x}_4]$, could be saved in LUT. Table 1 gives an example of LUT generated by minimizing the decomposition variance:

$$\phi(x|f) = \sum_i^2 m_{ii}, M = 1/J(x|f),$$

where $J(x|f)$ is the Fisher information matrix of decomposed material length and $m_{ii}$ is the diagonal element of matrix M. In this table, two flux scenarios (low fluxes and high fluxes) and two spectrum scenarios (soft and hard) are given, with total four cases. Please note that the LUT is not limited to only have four cases, and could have multiple scenarios for fluxes and spectrum.

TABLE 1

LUT used for switching the anode configuration and circuitry operation conditions

|  | Soft spectrum[2]<br>$f_2 \leq F_2$ | Hard spectrum<br>$f_2 > F_2$ |
|---|---|---|
| Low flux[1]<br>$f_1 \leq F_1$ | Pixel Size[3]: $\hat{x}_1 = 1$<br>CSP decay or reset time[4]:<br>($\hat{x}_2 = T_{11}$)<br>Shaping Time[5]:<br>($\hat{x}_3 = S_{11}$)<br>Comparator Voltage thresholds[6]: ($\hat{x}_4 = V_{11}$) | Pixel Size: $\hat{x}_1 = 1$<br>CSP decay or reset time:<br>($\hat{x}_2 = T_{12}$)<br>Shaping Time:<br>($\hat{x}_3 = S_{12}$)<br>Comparator Voltage thresholds: ($\hat{x}_4 = V_{12}$) |
| High flux:<br>$f_1 > F_1$ | Pixel Size: $\hat{x}_1 = 0$<br>CSP decay or reset time:<br>($\hat{x}_2 = T_{21}$)<br>Shaping Time:<br>($\hat{x}_3 = S_{21}$)<br>Comparator Voltage thresholds:<br>($\hat{x}_4 = V_{21}$) | Pixel Size: $\hat{x}_1 = 0$<br>CSP decay or reset time:<br>($\hat{x}_2 = T_{22}$)<br>Shaping Time:<br>($\hat{x}_3 = S_{22}$)<br>Comparator Voltage thresholds:<br>($\hat{x}_4 = V_{22}$) |

Notes:
1. Threshold $F_1$ is used to define the high flux and low flux case, typically in the range of 1 Mcps/mm$^2$ to 200 Mcps/mm$^2$.
2. Threshold $F_2$ is used to determine whether the spectrum is soft or hard. It can use ratio between the number of low and high energy x-rays, typically in the range of 0.1 to 10.
3. Pixel size $\hat{x}_1=1$ indicates that the circuitry is arranged with the large anode pixel and 0, with the small pixel.
4. CSP decay or reset time, $\hat{x}_2$ is in the range of 5 ns to 100 ns; typically, $T_{21}<T_{22}<T_{11}<T_{12}$
5. Shaping time, $\hat{x}_3$ is in the range of 5 ns to 100 ns; typically, $S_{21}<S_{22}<S_{11}<S_{12}$
6. Comparator voltage thresholds, $\hat{x}_4$, correspond to the photon energy within 0 keV to 160 keV; typically, $V_{11}<V_{21}<V_{12}<V_{22}$ Processor 53 controls the registers and outputs the switching signal and parameter signals based upon the contents of the registers and the information in the LUT. In a first operation, processor 53 receives an instruction from the sequence control (i.e., scan control circuit 33) that imaging for a view is ready and then resets the registers. Next, after a predetermined delay, the system performs the sensing operation to expose the subject to the sensing x-rays. Data from the adjustable photon counting circuits 42-1 to 42-n are stored in the set of registers. The processor compares the data in the registers with the information in the LUT and outputs a switching signal to switch 41 and parameter signals to the adjustable photon counting circuits 42-1 to 42-n such as the integration or delay time of the pre-amplifiers, shaping circuit parameters and reference voltage levels. For example, if the flux values are larger than a preset threshold value, the processor outputs a switching signal to configure the anodes in the small pixel mode, CSP using a shorter decay or reset time, filter/shaper with a shorter shaping time, and comparators with higher thresholds settings that can capture pile up effects better. Conversely, if the flux values are lower the preset threshold value, then the processor outputs a switching signal to configure the anodes together in the large pixel mode, CSP using a longer decay or reset time, filter/shaper with a longer shaping time, and comparators with lower thresholds settings. The threshold value will depend on the size of the anodes and the number anodes in a group. Specific parameters' value for CSP, filter and comparator thresholds are typically in the range of 5 ns to 100 ns (CSP), 5 ns to 100 ns (Shaper), 0 keV to 160 keV (comparator thresholds), respectively and will be precalculated and dependent on the object function ($\phi(x|f)$), which can be specifically designed base on system and design requirement, such as material decomposition variance, material decomposition bias, or mean square error.

Once the switch 41 and adjustable photon counting electronics 42-1 to 42-n are optimally set, the sequence control instructs the system to expose the subject for a given time with selected scan parameters over the view and collect exposure data. Once the exposure is completed, the processor instructs the registers to output the data.

The system according to the first embodiment optimally arranges the anodes spatially over the entire detector. The arrangement can have both small and large pixels configured to optimally acquire data from the x-ray exposure. Similarly, the associated settings for the photon counting circuits, shaping circuits and reference voltages are also arranged spatially over the entire detector. The detector can be spatially optimized to collect exposure data.

In a modification of the above embodiment, instead of each sensing circuit having a processor and LUT, the circuitry can be arranged to have one central processor with an LUT that processes the sensing data from all of the registers. As a second modification, several processors may be arranged to process a given number of registers. These two modifications have less circuitry.

The detector has non-uniform spatial sampling. The data can be processed to compensate for the non-uniform spatial sampling to achieve uniform sampling. In one approach, the large pixel data can be up-sampled to the high resolution of the small pixel. In a second approach, the small pixel data will be combined to the lower resolution of the large pixel through down-sampling. A third approach is to use a reconstruction algorithm to process the non-uniform sampling. This reconstruction algorithm can be typical iteratively reconstruction method and it can reconstruct the imaging object which is uniformly sampled from the non-uniform detector sampling data. The up-sampling, down-sampling and reconstruction algorithm are performed in the preprocessing circuitry 34.

The system according to the invention provides several advantages. Compared with conventional uniform pixel pitch design, the adaptive pixel configuration maintains good information in both high and low flux scenario, with ignorable dose penalty. The adaptive pixel configuration also allows the detector to always work in an optimal mode, improving the information collection efficiency, and detector response while reducing overall radiation dose and pile-up problems. Further, the overall power consumption can be reduced because the low flux regions are switched to the large pixel mode and the total number of active channels are reduced. This will reduce thermal the management effort in photon counting CT, which is always one of the major hurdles to develop efficient photon counting CT.

In a second embodiment of the system, different photon counting circuitry may be used. The system is not limited to the embodiment above using pre-amplifiers, shaping circuitry and voltage comparators. The adaptive pixel configuration may be used to optimize the performance of such other photon counting circuitry designed without shaping circuitry or without pixel switching circuitry. Generally speaking, leaving out shaping or switching will degrade the detector performance but may simplifying the circuitry.

The switching circuits 41, adjustable photon counting circuits 42-n and the processing circuit 43 for the entire detector are preferably implemented as an ASIC. Other configurations using separate circuit components are also possible.

Figure 9:
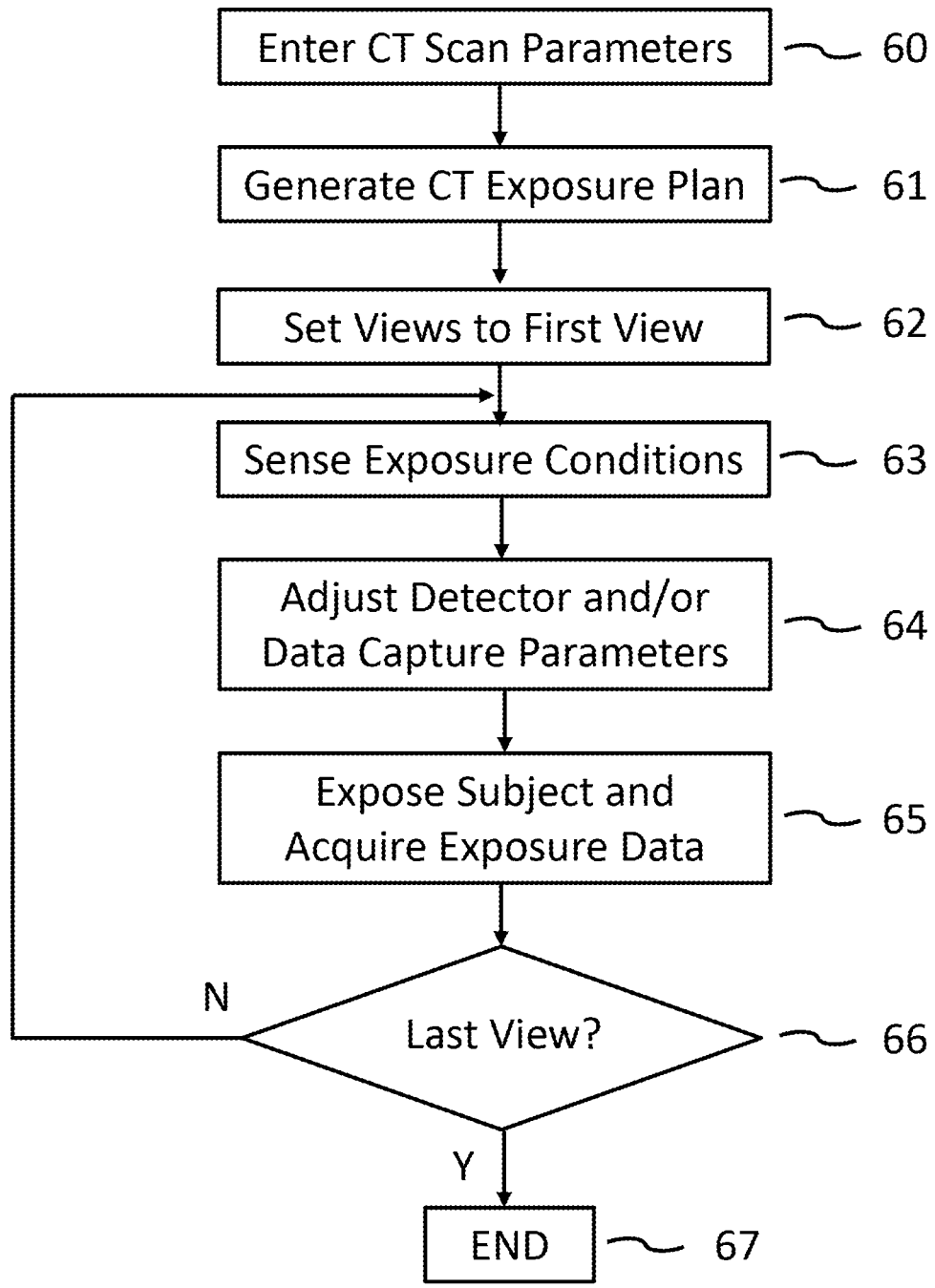
FIG. 9 is a flow diagram of the method according to an embodiment of the invention.

A first embodiment of the method according to the invention is shown in FIG. 9. A user operates the input circuitry by, for example, entering commands, instructions, and/or parameters via a keyboard or touch screen (step 60). The CT apparatus generates an exposure plan to scan a subject over a plurality of views in step 61. For each view beginning with the first view (step 62), in a first period the CT apparatus conducts a sensing operation to sense the flux and energy of the x-ray. The subject is exposed for a short amount of time to minimize exposure dose, such as a few tens of microseconds, the dose of which is, for example, <1% of dose used to generate the exposure data. The detector captures the sensing exposure data (flux and energy) and the photon counting circuits generates the collected data in the energy bins (step 63).

From the sensing exposure data the CT apparatus, in a second period, sets an optimal photon-counting mode. The setting of optimal mode includes setting an optimal pixel configuration over the entire detector geometry by spatially selecting optimal pixel sizes, and spatially setting optimal pre-amplifier, shaping and energy comparator threshold settings over the entire detector geometry (step 64). One or more of these parameters are adjusted to obtain optimal exposure acquisition. The selection process can be achieved using a look-up table (LUT) populated with predetermined settings derived empirically or derived experimentally through a calibration process using known samples and/or sample materials. The second period typically in the range of 1 ns to 1 μs.

In a third period, the subject is exposed over the view and the exposure data is acquired (step 65). The acquisition typically lasts on the order of hundreds to thousands of microseconds. As such, the dose penalty for the sensing and parameter setting is only about 1%. The exposure data The sensing, parameter setting and data acquisition procedures are repeated for each view until the last view is reached (step 66) and the procedure ends (step 67).

Figure 10:
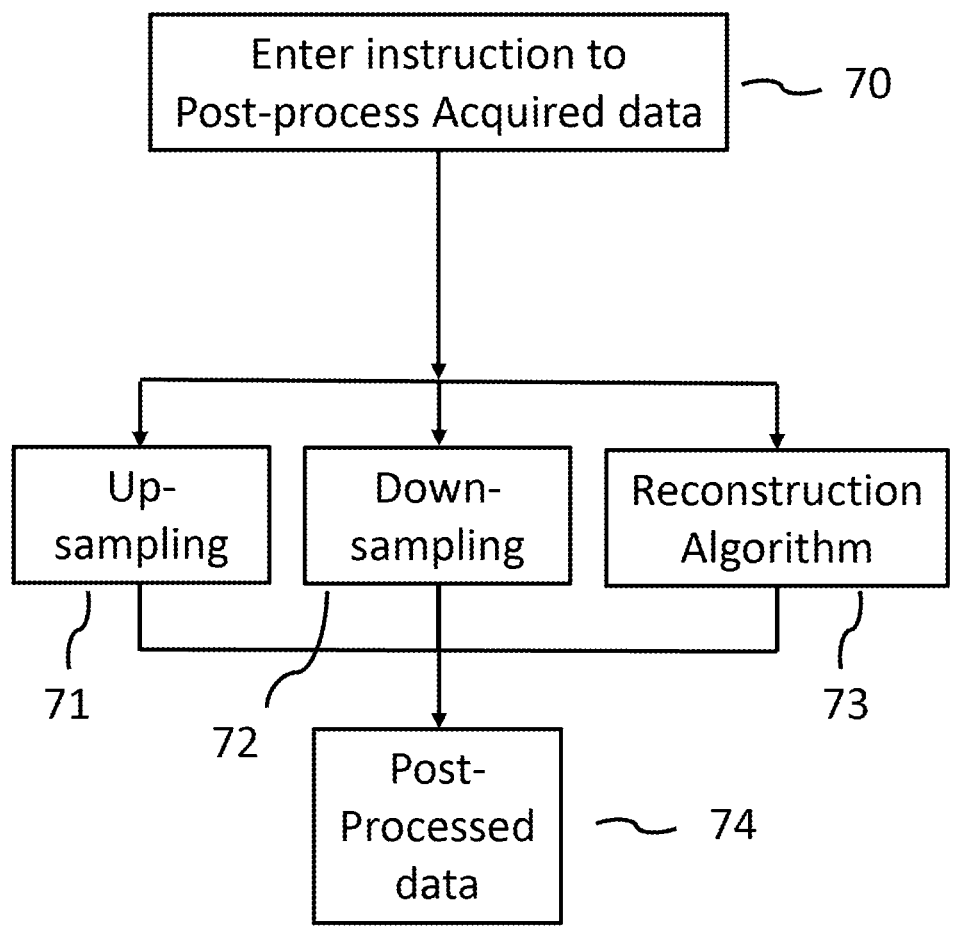
FIG. 10 is a flow diagram of post-processing of acquired data.

FIG. 10 shows further steps of the method according to the invention. After acquiring the exposure data in step 65 for all of the views, the user of the system can enter an instruction for the acquired data to be post-processed (step 70). The acquired data is processed by up-sampling (step 71), down-sampling (step 72) or by running a reconstruction algorithm (step 73) according to the instruction. Post-processed data is obtained (step 74).

What is claimed is:

1. A computed tomography apparatus, comprising:
   an x-ray source;
   scan control circuitry configured to control the x-ray source to expose a subject with x-rays over a scan having a plurality of views;
   a detector disposed to receive x-rays from the x-ray source and having plurality of anodes arranged in groups;
   photon counting circuits respectively provided for each of the anodes and having adjustable operating parameters;
   connection circuitry configured to adaptively connect, in a first mode, each anode to one of the photon counting circuits and, in a second mode, each anode in a group to a same one of the photon counting circuits; and
   processing circuitry, connected to the connection circuitry and the photon counting circuits, configured to, for each of the views, select the first mode or the second mode and adjust the operating parameters based upon exposure data obtained from exposing the subject with the x-rays from the x-ray source.

2. The computed tomography apparatus according to claim 1, wherein:
   scan control circuitry configured to control the x-ray source to expose the subject with the x-rays over the scan, the scan including a first exposure before a second exposure; and
   the processing circuitry is configured to select the first mode or second and adjust the operating parameters based upon the first exposure.

3. The computed tomography apparatus according to claim 2, wherein:
   the first exposure has a duration and an x-ray exposure level each less than that of the second exposure.

4. The computed tomography apparatus according to claim 2, wherein:
   each of the photon counting circuits is configured to determine a number of photons and an energy distribution of the photons for a corresponding anode during the first exposure.

5. The computed tomography apparatus according to claim 2, wherein:
   the processing circuitry comprises:
     a processor, and
     a storage containing mode data and operating parameter data as a function of x-ray flux and energy;
   the processor is configured to compare data from the first exposure of the scan with data in the storage to select the first mode or the second mode and adjust the operating parameters; and
   the scan control circuitry is configured to control the x-ray source to expose the subject with x-rays during the second exposure of the scan using the selected mode and adjusted operating parameters from the comparison based upon the data from first exposure of the scan.

6. The computed tomography apparatus according to claim 5, wherein the storage is a look up table.

7. The computed tomography apparatus according to claim 1, wherein the processing circuitry is configured to:
   generate exposure data; and
   process the exposure data to increase spatial uniformity.

8. The computed tomography apparatus according to claim 7, where the processing circuitry is configured to down-sample data collected from the anodes connected to one of the photon counting circuits and up-sample data connected from anodes connected in the group.

9. The computed tomography apparatus according to claim 1, wherein the photon counting circuitry comprises:
   a charge sensitive preamplifier which outputs a pulse signal having a shape and a width; and
   shaping circuitry configured to adjust at least one of the shape and width of the pulse signal.

10. The computed tomography apparatus according to claim 9, wherein the processing circuitry is configured to adjust at least one of an integration time of the charge sensitive preamplifier and a pulse width of the shaping circuitry based upon the exposure data.

11. The computed tomography apparatus according to claim 9, wherein the shaping circuitry is configured to adjust at least one of the shape and width of the pulse signal based upon at least one of x-ray energy and flux.

12. The computed tomography apparatus according to claim 1, comprising a common conductive strip disposed between the anodes having a lower applied voltage that that of the anodes.

13. A photon counting computed tomography method, comprising:
   exposing a subject with x-rays over a scan having a plurality of views, each of the views having a first exposure period before a second exposure period;
   determining an energy distribution of x-ray received during the first exposure period using photon counting circuitry and a detector having a plurality of anodes arranged in groups, for each of the plurality of views;
   selecting a number of anodes in each group and operating parameters of the photon counting circuitry based upon the x-rays received during the first exposure period; and
   exposing the subject during the second period based upon the selected number of anodes and operating parameters.

14. The photon counting computed tomography method according to claim 13, wherein said first exposure period has a duration and an x-ray exposure level each less than that of the second exposure period.

15. The photon counting computed tomography method according to claim 13, comprising:
   comparing the energy distribution to mode data and operating parameter data stored as a function of x-ray flux and energy; and
   selecting the number of anodes in each group and the operating parameters of the photon counting circuitry based upon the comparing.

16. The photon counting computed tomography method according to claim 13, comprising:
   exposing the subject to a level of x-rays during the first period designed to sense x-ray flux and energy of the view; and
   exposing the subject to a level of x-rays during the second period designed to generate image data of the view.

17. The photon counting computed tomography method according to claim 13, comprising:
   generating exposure data from exposing the subject during the second exposure period; and
   processing the exposure data to increase spatial uniformity.

18. The photon counting computed tomography method according to claim 13, comprising:
   down-sampling data collected from the anodes connected to one of the photon counting circuitry; and
   up-sampling data collected from the anodes connected as a group to the photon counting circuitry.

19. The photon counting computed tomography method according to claim 13, wherein the photon counting circuitry comprises:
- a charge sensitive preamplifier which outputs a pulse signal having a shape and a width; and
- shaping circuitry configured to adjust at least one of the shape and width of the pulse signal, the method comprising:
- adjusting at least one of an integration time of the charge sensitive preamplifier and a pulse width of the shaping circuitry based upon the exposure data.

20. The photon counting computed tomography method according to claim 13, comprising:
- disposing a common electrode strip between the anodes in a group; and
- applying a voltage to the strip less than that applied to the anodes.

* * * * *